(12) United States Patent
Bunch et al.

(10) Patent No.: US 11,179,178 B2
(45) Date of Patent: Nov. 23, 2021

(54) VAGINAL POSITIONER FOR UTERINE TAMPONADE DEVICE AND METHODS OF USING THE SAME

(71) Applicant: Cook Medical Technologies LLC, Bloomington, IN (US)

(72) Inventors: Kristen M. Bunch, Bloomington, IN (US); Victor Havill, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 18 days.

(21) Appl. No.: 16/046,327

(22) Filed: Jul. 26, 2018

(65) Prior Publication Data

US 2019/0059947 A1 Feb. 28, 2019

Related U.S. Application Data

(60) Provisional application No. 62/552,486, filed on Aug. 31, 2017.

(51) Int. Cl.
*A61B 17/42* (2006.01)
*A61B 17/12* (2006.01)
(Continued)

(52) U.S. Cl.
CPC ........ *A61B 17/42* (2013.01); *A61B 17/12099* (2013.01); *A61B 17/12136* (2013.01); *A61B 17/06061* (2013.01); *A61B 2017/00477* (2013.01); *A61B 2017/00557* (2013.01); *A61B 2017/00902* (2013.01);
(Continued)

(58) Field of Classification Search
CPC .............. A61B 17/42; A61B 17/12099; A61B 17/12136; A61B 17/06061; A61B 2017/00477; A61B 2017/00557; A61B 2017/00902; A61B 2017/12004;
(Continued)

(56) References Cited

U.S. PATENT DOCUMENTS

| 837,085 A | 11/1906 | Loar |
| 3,822,702 A | 7/1974 | Bolduc |

(Continued)

FOREIGN PATENT DOCUMENTS

| DE | 4225520 A1 | 2/1994 |
| JP | 2014100303 A | 6/2014 |

(Continued)

OTHER PUBLICATIONS

Search Report and the Written Opinion for PCT/US2019/051100, dated Feb. 11, 2020, 18 pages.

(Continued)

*Primary Examiner* — Jing Rui Ou
(74) *Attorney, Agent, or Firm* — Crowell & Moring LLP

(57) ABSTRACT

A device for use with a uterine tamponade apparatus, such as the Bakri® postpartum hemorrhage balloon, is disclosed. The device comprises an anchor for deployment within the vagina to securely retain the balloon in its proper position within the uterine cavity, allowing the balloon to function as intended for the control and management of postpartum hemorrhage and uterine bleeding. Methods of use of the vaginal anchor are also disclosed.

12 Claims, 5 Drawing Sheets

(51) Int. Cl.
*A61B 17/00* (2006.01)
*A61B 17/06* (2006.01)

(52) U.S. Cl.
CPC .............. *A61B 2017/12004* (2013.01); *A61B 2017/1205* (2013.01); *A61B 2017/4216* (2013.01); *A61B 2017/4225* (2013.01)

(58) Field of Classification Search
CPC .... A61B 2017/1205; A61B 2017/4216; A61B 2017/4225
See application file for complete search history.

(56) References Cited

U.S. PATENT DOCUMENTS

| | | | |
|---|---|---|---|
| 4,207,891 A | 6/1980 | Bolduc | |
| 4,402,684 A | 9/1983 | Jessup | |
| 4,601,698 A * | 7/1986 | Moulding, Jr. | A61F 6/225 128/831 |
| D286,677 S | 11/1986 | Osborne | |
| 4,753,640 A | 6/1988 | Nichols et al. | |
| 4,964,854 A | 10/1990 | Luther | |
| 5,295,968 A | 3/1994 | Martel et al. | |
| 5,569,222 A | 10/1996 | Haselhorst et al. | |
| 6,135,982 A | 10/2000 | Campbell | |
| 6,245,029 B1 | 6/2001 | Fujita et al. | |
| 6,395,012 B1 | 5/2002 | Yoon et al. | |
| D476,418 S | 6/2003 | Sprieck | |
| 6,740,095 B2 | 5/2004 | Watson | |
| 6,813,520 B2 * | 11/2004 | Truckai | A61B 18/1485 600/372 |
| D565,192 S | 3/2008 | Tajima | |
| D585,547 S | 1/2009 | Basleri | |
| 7,512,433 B2 | 3/2009 | Bernhart | |
| D630,733 S | 1/2011 | Ahlgren | |
| D640,785 S | 6/2011 | Lee | |
| D663,832 S | 7/2012 | Essinger | |
| 8,282,612 B1 | 10/2012 | Miller | |
| 8,287,496 B2 | 10/2012 | Racz | |
| D692,134 S | 10/2013 | Lee-Sepsick | |
| D699,341 S | 2/2014 | Clark | |
| 8,770,200 B2 | 7/2014 | Ahluwalia | |
| D713,957 S | 9/2014 | Woehr | |
| 9,028,401 B1 | 5/2015 | Bacich et al. | |
| 9,067,013 B2 | 6/2015 | Wright et al. | |
| D747,802 S | 1/2016 | Freigang | |
| D748,777 S | 2/2016 | Uenishi | |
| D751,704 S | 3/2016 | Corydon | |
| 9,364,638 B2 | 6/2016 | Duncan | |
| D772,411 S | 11/2016 | Heath | |
| D798,446 S | 9/2017 | Nino | |
| D816,217 S | 4/2018 | Naughton | |
| D846,116 S | 4/2019 | Naughton | |
| D854,148 S | 7/2019 | Prinz | |
| D859,651 S | 9/2019 | Harding | |
| 2004/0030352 A1 | 2/2004 | McGloughlin et al. | |
| 2004/0267203 A1 | 12/2004 | Potter | |
| 2005/0143689 A1 | 6/2005 | Ramsey, III | |
| 2005/0149060 A1 | 7/2005 | Thorstenson | |
| 2005/0256532 A1 | 11/2005 | Nayak | |
| 2006/0015075 A1 | 1/2006 | Blanco | |
| 2006/0173486 A1 | 8/2006 | Burke et al. | |
| 2009/0112167 A1 | 4/2009 | Haarala et al. | |
| 2009/0157007 A1 | 6/2009 | McKinnon | |
| 2011/0060317 A1 | 3/2011 | Frojd | |
| 2011/0220120 A1 | 9/2011 | Frigstad et al. | |
| 2011/0259344 A1 * | 10/2011 | Ahluwalia | A61B 90/04 128/834 |
| 2013/0204208 A1 | 8/2013 | Olson et al. | |
| 2014/0094773 A1 | 4/2014 | Lampropoulos | |
| 2014/0158138 A1 | 6/2014 | Ziv et al. | |
| 2015/0051634 A1 | 2/2015 | Kravik et al. | |
| 2015/0202411 A1 | 7/2015 | Duncan | |
| 2015/0342641 A1 | 12/2015 | Belfort et al. | |
| 2016/0045719 A1 | 2/2016 | Ha et al. | |
| 2016/0100861 A1 | 4/2016 | Parys et al. | |
| 2016/0106466 A1 | 4/2016 | Gruber et al. | |
| 2016/0151049 A1 | 6/2016 | Massengale | |
| 2016/0166282 A1 | 6/2016 | Juravic et al. | |
| 2016/0256301 A1 | 9/2016 | Roeder | |
| 2017/0312432 A1 | 11/2017 | Huang | |
| 2018/0256389 A1 * | 9/2018 | Asfar | A61F 6/08 |
| 2018/0360494 A1 | 12/2018 | Melsheimer | |
| 2019/0059947 A1 | 2/2019 | Bunch et al. | |
| 2019/0110797 A1 | 4/2019 | Melsheimer | |

FOREIGN PATENT DOCUMENTS

| | | |
|---|---|---|
| WO | WO 00/57943 A1 | 10/2000 |
| WO | WO 2014/054156 A | 8/2016 |

OTHER PUBLICATIONS

Examination Report for Australian Application No. 2018288595, dated Apr. 20, 2020, 5 pages.
Partial International Search Report for PCT/US2018/036865, dated Aug. 31, 2018, 10 pages.
International Search Report and Written Opinion for PCT/US2018/036865, dated Oct. 23, 2018, 18 pages.
International Preliminary Report on Patentability and Written Opinion for PCT/US2018/036865, dated Dec. 24, 2019, 8 pages.
Invitation to Pay Additional Fees and Communication Relating to the Results of the Partial International Search for PCT/US2019/051100, dated Dec. 16, 2019, 11 pages.
Examination Report for EP Application No. 18738046.4, dated Dec. 14, 2020, 4 pages.
Office Action and English translation for Japanese application No. 2019-570104, dated Jan. 20, 2021, 12 pages.
Office Action and English translation of Korean Application No. 10-2020-7001142 dated Jun. 9, 2021, 11 pages.
International Preliminary Report on Patentability for PCT Application No. PCT/US2019/051100, dated Mar. 23, 2021, 10 pages.
Office Action and English translation of Japanese Application No. 2019-570104, dated Jul. 26, 2021, 4 pages.

* cited by examiner

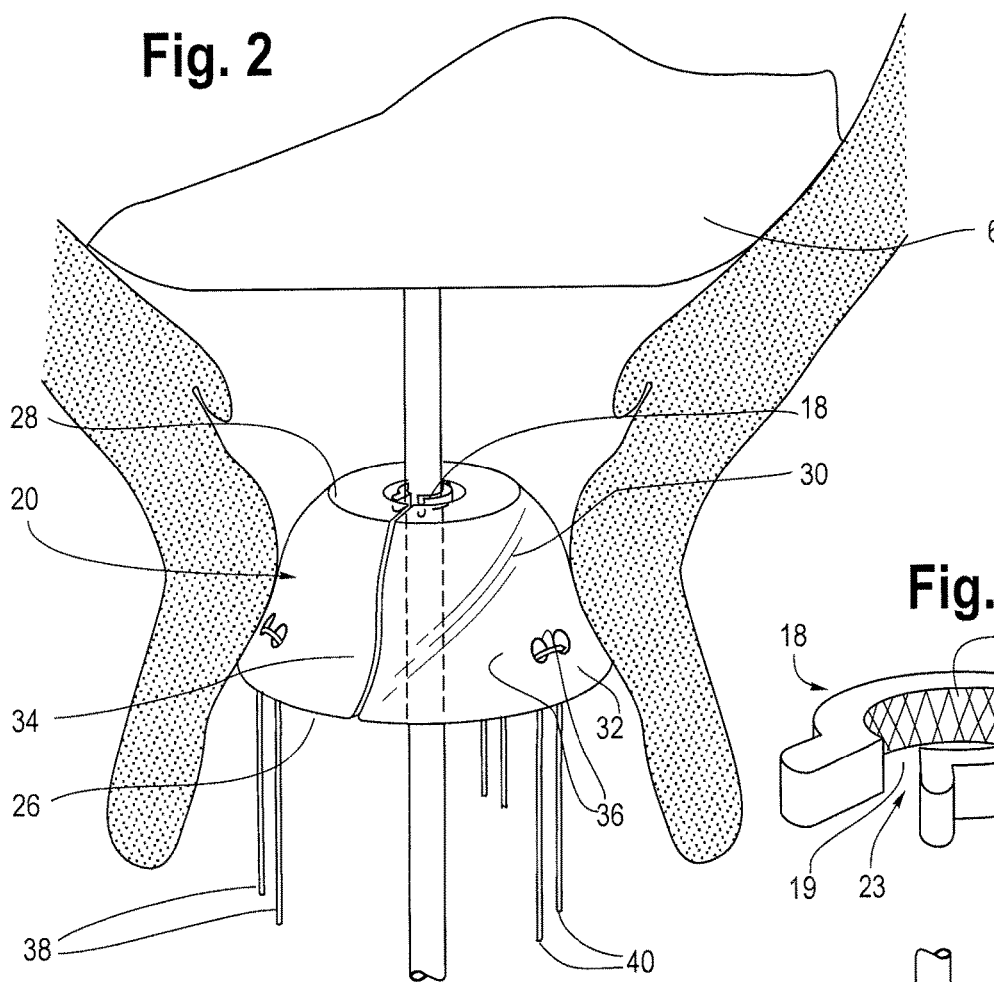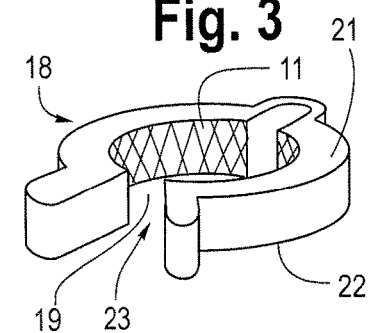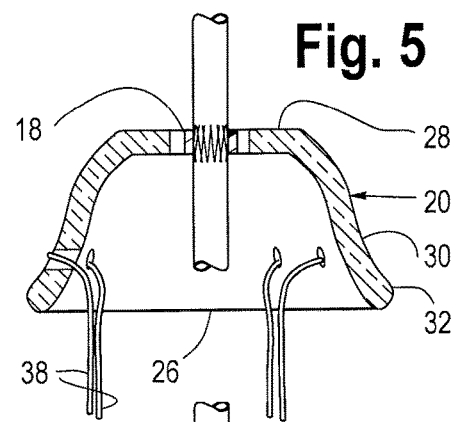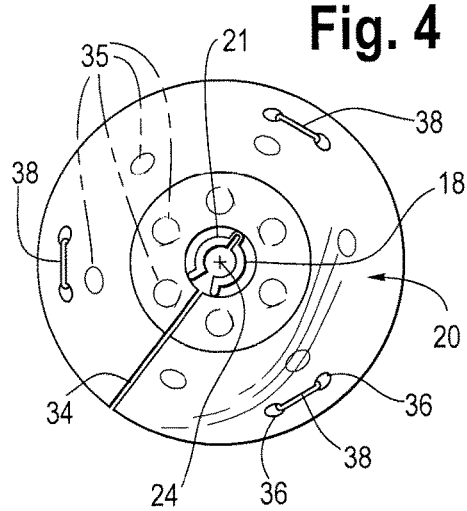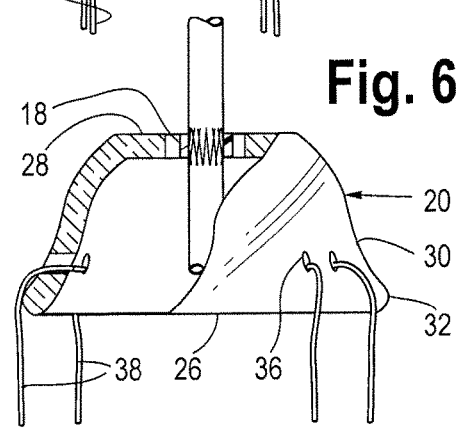

VAGINAL POSITIONER FOR UTERINE TAMPONADE DEVICE AND METHODS OF USING THE SAME

RELATED APPLICATIONS

This application claims the benefit of the filing date under 35 U.S.C. § 119(e) of Provisional U.S. Patent Application Ser. No. 62/552,486, filed Aug. 31, 2017, which is hereby incorporated by reference.

TECHNICAL FIELD

The present invention relates generally to apparatus and methods for controlling uterine bleeding, and more specifically, to a device for use with a uterine tamponade assembly that facilitates proper positioning and retention of the tamponade assembly within the uterus.

Uterine bleeding is a clinical condition attributable to a variety of causes, including postpartum hemorrhages (PPH) following vaginal and/or cesarean childbirth. Postpartum hemorrhage or excessive blood loss after birth is commonly caused by uterine atony whereby the uterus fails to contract normally after the delivery of a baby, leading to continuous bleeding. If left untreated, PPH may cause serious complications or even death.

There are a variety of techniques used for treating and managing PPH, including the administration of muscle contracting drugs or agents alone or in combination with other mechanical or surgical techniques. One such technique includes inserting a tamponade apparatus, such as a balloon catheter into the uterus, wherein the balloon is inflated to a sufficient pressure and volume until it conforms generally to the contour of the uterine cavity. The application of pressure to the interior uterine wall provides a tamponade effect until bleeding is controlled or stopped. One example of a uterine tamponade balloon catheter is the Bakri® balloon, Cook Medical, Bloomington, Ind. The effectiveness of the Bakri® balloon may be partially attributable to maintaining the balloon in a proper position within the uterine cavity, and more specifically, in the lower uterine segment.

In most cases, the balloon stays in place in the uterus during treatment as long as the balloon was inserted properly. However, in some instances, the uterus may try to "deliver" or expel the balloon through an insufficient or dilated cervix and into the vagina, thereby requiring the balloon to be deflated and reinserted. Thus, it is desirable to prevent full or partial dislodgement of the balloon from the uterus, by providing a device located in the vagina which anchors the balloon catheter in a desired position within the uterus. Accordingly, the disclosed device can be used with various known uterine tamponade devices, such as the Bakri® balloon. The disclosed device may be deployed within the vagina to securely retain the balloon in its proper position within the uterine cavity, allowing the balloon to function as intended for the control and management of PPH and uterine bleeding.

SUMMARY

The present disclosure provides an apparatus and method for securely anchoring a uterine tamponade device in its proper position within the uterine cavity. In one example, a uterine tamponade assembly is disclosed. The assembly comprises a catheter comprising a longitudinal body having a proximal end and a distal end and at least one drainage lumen extending there between. An expandable tamponade device is located at the distal end of the catheter, and is configured for insertion into a body cavity. The assembly also comprises an anchor for securing the assembly within the body cavity. The anchor comprises at least one clip removably attached to the longitudinal catheter body and at least one outer disk disposed about the at least one clip.

The present disclosure also provides for a vaginal anchor for securing a balloon catheter in the uterine cavity comprising. In one example, the anchor comprises an inner clip and an outer ring comprising a proximal end and a distal end and a sidewall extending there between, wherein the sidewall defines a center lumen extending between the proximal and distal ends. The inner clip is at least partially housed within the lumen at the distal end of the outer ring and comprises a slot and wherein the outer ring comprises a slit formed in the sidewall that is substantially aligned with the slot formed in the inner clip.

The present disclosure also provides for a method of retaining a tamponade balloon catheter in the uterine cavity. In one example, the method comprises attaching a vaginal anchor on a longitudinal shaft of a balloon catheter, the anchor comprising an inner clip and an outer ring comprising a proximal end and a distal end and a sidewall extending there between. The sidewall defines a center lumen extending between the proximal and distal ends and the inner clip is at least partially housed within the lumen at the distal end of the outer ring. The inner clip comprises a slot and the outer ring comprises a slit formed in the sidewall that is substantially aligned with the slot formed in the inner clip. The method further comprises sliding the anchor longitudinally on the catheter shaft into a desired location within the vaginal canal.

BRIEF DESCRIPTION OF THE DRAWINGS

FIG. 2 is an enlarged perspective view of one example of an anchor secured to a catheter shaft and deployed in the vagina with multiple tethers extending out of the body.

FIG. 3 is one example of an inner clip 18 portion of the anchor shown in FIG. 2.

FIG. 4 is a top view of the anchor of FIG. 2 including an inner clip 18 and outer ring and optional drainage openings.

FIG. 5 is a side cross-sectional view of the anchor of FIG. 2.

FIG. 6 is a side partial cut-away view of the anchor of FIG. 2 showing details of the tethers threaded through pairs of holes formed in the outer ring of the anchor.

DETAILED DESCRIPTION

Throughout this specification, the terms proximal and proximally are used to refer to a position or direction away from, or even external to a patient's body and the terms distal and distally are used to refer to a position or direction towards the patient and/or to be inserted into a patient's body orifices or cavities. The embodiments described below are primarily in connection with a device for use with, or as an accessory to, a tamponade device such as a balloon catheter for treating postpartum hemorrhage, and for anchoring the balloon catheter in a desired position within the uterus. However, the described device may also be used in connection with a range of medical instruments which are inserted into various body cavities to maintain the position of such instruments depending on the technique or procedure being performed as will be appreciated by those of skill in the art.

Figure 1:
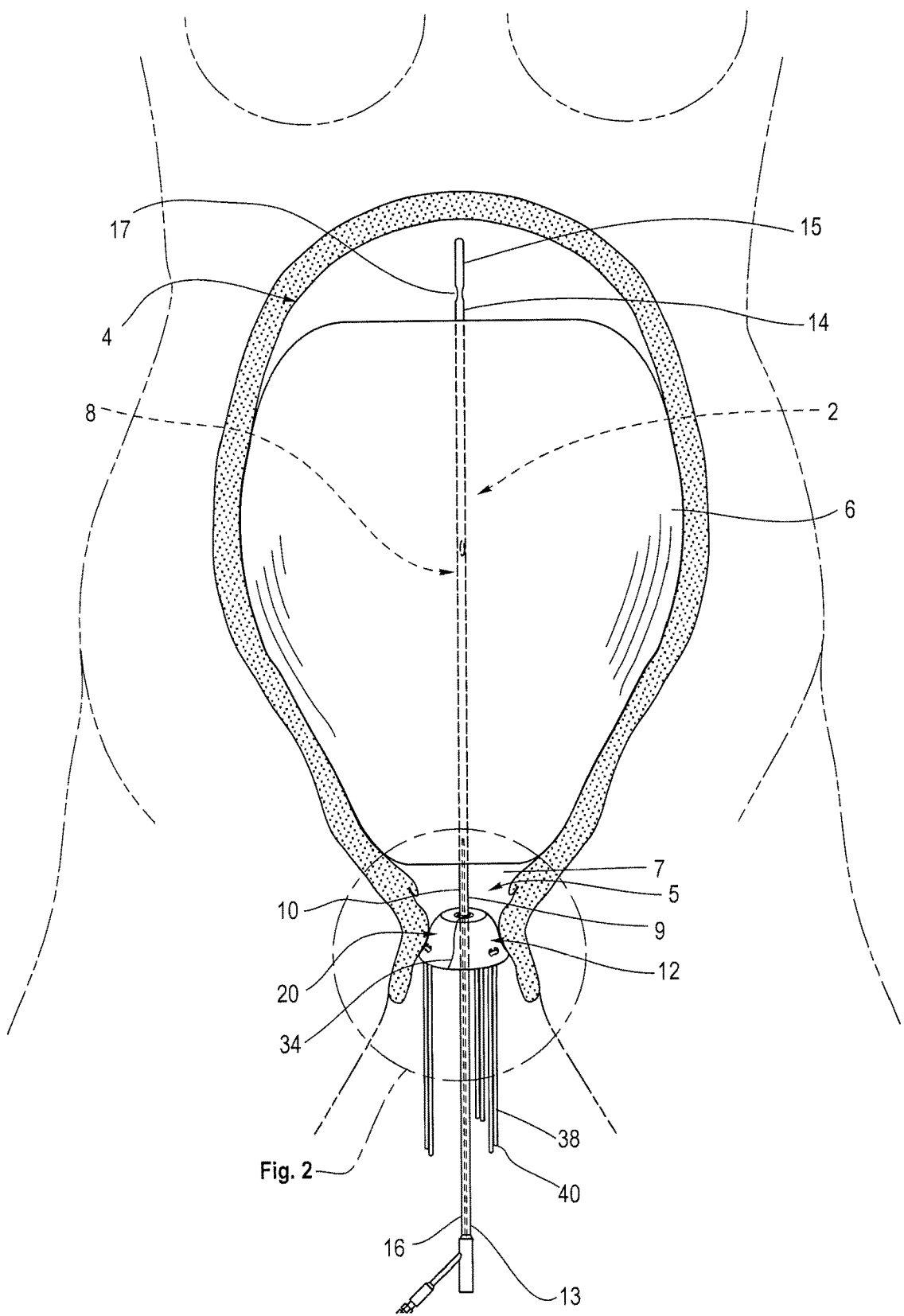
FIG. 1 is a front view of a patient's anatomy showing a uterine tamponade device and one example of an anchor deployed in the vagina for anchoring the tamponade device in place within the uterine cavity.

FIG. 1 illustrates one example of a uterine tamponade assembly 2 positioned within a patient's anatomy. Tamponade, which is the closure or blockage of a wound by applying direct pressure to the source of bleeding, is a useful method of stopping or managing bleeding or hemorrhage. One example of a known tamponade assembly includes a Bakri® balloon catheter (Cook Medical, Bloomington, Ind.). The tamponade assembly 2, i.e., Bakri® balloon catheter, is shown as being expanded within the uterine cavity and is shown as being equipped with a retention device or anchor 12 deployed in the vagina 5 for anchoring the balloon catheter 2 in place within the uterine cavity 4. While the balloon catheter 2 is intended for placement in the uterine cavity 4 of a patient for treating and controlling postpartum hemorrhage (PPH), it may also be used in various other locations, lumens or orifices within the body, including vessels, bones, organs or other tissues, as necessary or desired. Its dimensions are alterable so that it may be appropriately dimensioned to navigate to the uterus 4, or any other target body cavity, from which fluid, such as blood, will be drained.

As shown in FIG. 1, the tamponade assembly 2 preferably includes a catheter 8 having a longitudinal shaft 9 and a distal end 15 and a proximal end 13. There is a drainage lumen 16 extending along the length of the longitudinal shaft 9 between the proximal 13 and distal 15 ends and, in one example, a connector (such as a Y-connector or any other suitable connector) may be located at the proximal end 13 of the catheter 8 for connecting the catheter to a collection bag or receptacle for receiving fluid and/or blood drained from the patient. The catheter 8 may include one or more openings 17 at or near its distal end 15, such that when the distal end 15 of the catheter 8 is positioned in the uterus 4, the openings 17 allow blood and other fluids to enter and flow through the drainage lumen 16. The drainage lumen may also be used to introduce irrigation fluid or other material into the uterus, such as to flush the openings 17 at the distal end 15 of the catheter 8 should they become blocked with clotted blood, tissue or other debris. The catheter 8 may also include additional ports or orifices at various points along the longitudinal shaft 9 to allow blood or other fluid to enter the catheter 8.

A tamponade device 6, such as a balloon, is located near the distal end 15 of the catheter 8, and is preferably made of an expandable material such as rubber, silicone, latex or any other expansible biocompatible material. Other tamponade mechanisms may also be used in lieu of or in addition to the balloon 6, such as plurality of arms, tubes, loops, mesh or similar structures capable of expanding or otherwise conforming to the uterine cavity 4. An inflation lumen 14 within the catheter 8 is provided to allow for inflation and deflation of the balloon 6. The inflation lumen 14 may run parallel with the drainage lumen 16, but preferably, the two lumens 16, 14 remain separate for their entire lengths. Various media, such as water, saline, air or other physiologically compatible medium may be introduced through the inflation lumen 14 to facilitate controlled expansion of the balloon 6.

Once the balloon 6 has been placed within the uterus 4 of the patient, the balloon 6 may be inflated or otherwise expanded. Preferably, the balloon 6 has sufficient compliance such that, when expanded, it conforms generally to the shape and contour of the cavity in which it is placed, and when deflated, can be sufficiently reduced in profile to provide for easy insertion and removal through the cervix 7 and vagina 5. The size and volume to which the balloon 6 may expand is preferably determined by the body cavity where hemorrhage control is needed. As shown in FIG. 1, the balloon 6 is preferably inflated with a sufficient volume and pressure such that it conforms generally to the contours of the uterine cavity 4, and more specifically, to the lower uterine segment. In one example, when using a balloon 6 such as the Bakri® balloon, the balloon 6 may be inflated with up to about 500 ml of saline. In other examples, if other types or sizes of balloons are used, the inflation volume may be more or less. The inflated balloon 6 then exerts a generally uniform compressive force or pressure upon the uterine wall to substantially reduce or even stop the uterine bleeding or hemorrhage. It may also be possible to coat or impregnate all or at least a portion of the balloon surface that comes into contact with the uterine wall with biocompatible materials, drugs or other substances that may enhance or assist in controlling uterine bleeding. In one non-limiting example, this may include muscle contracting or clotting enhancing drugs or other substances that facilitate inflation/deflation of the balloon 6.

As shown in FIG. 1, the catheter 8 may further include an internal stylet 10 to provide structure or added rigidity to the catheter 8. The stylet 10 may be integrally formed within the catheter or, alternatively, the stylet 10 may be inserted into the catheter 8 by a physician prior to or during use. Preferably, the stylet 10 extends longitudinally within the drainage lumen 16, or alternatively through the inflation lumen 14 or through an additional or separate lumen. In one non-limiting example, the internal stylet 10 may be a hollow vinyl tube with a lumen extending there through, which provides an additional drainage conduit through which blood or other fluids can flow. However, the stylet 10 may be a variety of other shapes and configurations, solid or hollow, and made of suitable biocompatible materials including plastics, metals and/or combinations thereof. The stylet 10 may run the entire length, or at least a portion of the length of the catheter 8, and extend to a location adjacent to or just distal of the openings 17 at the distal end 15 of the catheter 8, for example, or at least extend a sufficient length so as to add longitudinal stability to the catheter 8. The stylet 10 thereby reduces or substantially eliminates unwanted folding and/or bending of the catheter 8, while also resisting and preventing longitudinal shortening, shrinkage and/or collapse during trans-vaginal insertion (and/or insertion through C-section) and during positioning of the balloon 6 within the uterus 4.

Figure 7:
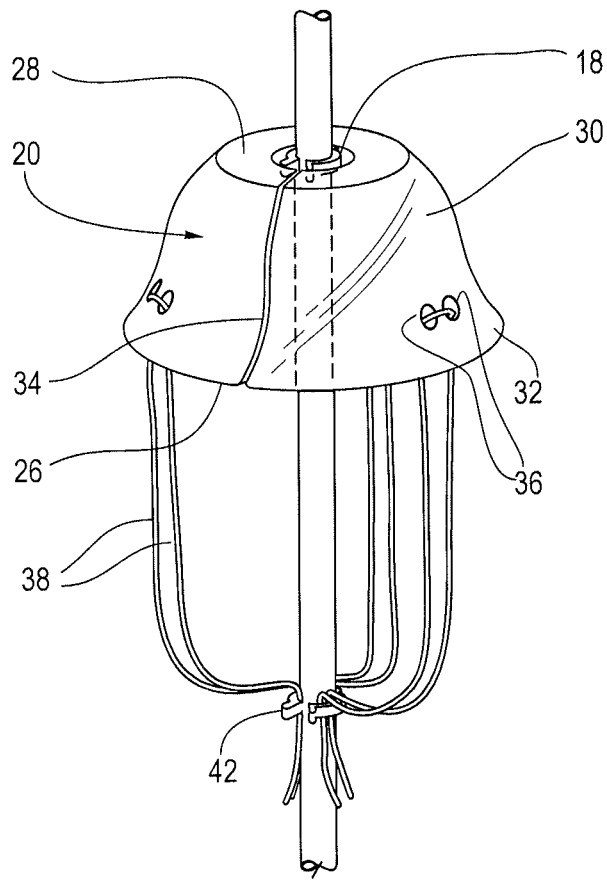
FIG. 7 is an enlarged perspective view of another example of an anchor secured to a catheter shaft with multiple tethers extending to an optional tether attachment ring.

As illustrated generally in FIGS. 1, 2 and 7, the assembly 2 includes a device to facilitate retention of the assembly 2 and prevent unintentional or unwanted dislodgement once the balloon 6 has been properly positioned and expanded within the uterus 4. In one example, the device is a retention mechanism such as anchor 12. The anchor 12 is preferably usable in connection with the balloon catheter assembly 2, and may be provided as an accessory thereto. It is also contemplated that the anchor 12 may be used in connection with other medical devices in which it is desirable to retain such devices in a particular position or location within a body cavity. As such, the anchor 12 is preferably removably attachable to the assembly 2 so that it can be attached or secured to the catheter 8 when needed, and also conveniently removed if desired. In one example, the anchor 12 can be snap-fitted onto the longitudinal catheter shaft 9 at a desired location, or otherwise removably attached such as by friction fit, adhesive or other suitable attachment mechanisms, while allowing the anchor 12 to remain slideably movable along the longitudinal shaft 9 of the catheter 8.

As shown generally in FIGS. 2-6, in one embodiment, the anchor 12 may comprise an inner clip 18 and an outer disk 20. In one example, the inner clip 18 may be relatively rigid compared to the outer disk 20. For example, the inner clip 18 may be made of a relatively harder and/or more rigid plastic, including but not limited to ABS, nylon and/or polyurethane blends and/or polycarbonate. The clip 18 may be a ring-like structure that fully surrounds or encircles the shaft 9 of the catheter 8 and can be threaded onto one end of the catheter 8 and pushed longitudinally or slid into position at a desired location on the catheter 8 for use. Alternatively, the clip 18 may fully or at least partially surround the shaft 9 of the catheter. For example, the clip 18 may comprise a generally ring-like structure with opposing facing or abutting arms that form a small opening or slot 23 between the opposing facing arms that allows the clip 18 to be snap fitted on (and off) of the catheter 8 from the side at any desirable location along the length of the shaft 9 of the catheter 8. In one example, the clip 18 may be constructed of a material that is rigid enough to allow the clip to maintain its overall structure and form to snugly fasten onto the catheter, but flexible enough to allow the opposing facing arms to be pulled or moved apart far enough to receive the longitudinal body 8 of the catheter 9 there between during attachment and removal of the anchor 12 from the catheter 9. However, in a resting position, the natural resiliency of the opposing facing arms of the inner clip 18 may result in the arms pulling slightly radially inwardly such that the arms are abutting or touching to form a substantially circular structure. The inner clip 18 may also comprise a horseshoe shape or semi-circular or curved shape that allows the inner clip 18 to be removably attached to the catheter 8.

In one example, the inner diameter of the clip 18 may be in the range of approximately 0.1 in. to 1.5 in., and more preferably, about 0.3 in. in order to wrap snugly around the outer diameter of the longitudinal shaft 9 of the catheter 8. However, it is also contemplated that the inner diameter of the clip 18 may be modified to a variety of shapes and dimensions so as to be usable and compatible with other sizes and diameters of catheter tubing or any other device to which it may be desirable to attach the clip 18. As shown in FIG. 3, the clip 18 has a top or distal end 21 and a bottom or proximal end 22 and a center opening 19. The clip 18 may have a smooth outer edge or surface and a roughened or textured inner surface 11 of the center opening 19 that serves to reduce or prevent slippage or dislodgment of the clip 18 on the longitudinal shaft 9 of the catheter 8. In one example, the roughened inner surface 11 may aid placement of the anchor 12 by including a textured design or pattern that glides smoothly when pushed up or distally into place on the shaft 9 of the catheter 8, but which resists sliding in the opposite (proximal) direction during use to enhance traction along the shaft 9, providing retention of the anchor 12 and preventing unwanted sliding or dislodgement of the anchor 12.

In addition to the inner clip 18, the anchor 12 may further include an outer disk 20 having a proximal end 26, a distal end 28 and a sidewall 30 extending there between. The disk 20 is generally shaped and configured to have a center opening 24 which surrounds or covers at least a portion of the inner clip 18. The outer diameter of the clip 18 may be about 7 cm or less, or at least a small enough outer diameter so as to fit within the center opening 24 of the outer disk 20. As shown in FIGS. 2-6, the clip 18 would be generally housed within the top or distal end 28 of the outer disk 20. As such, distal end 28 of the disk 20 may have an inner diameter that is slightly smaller than or just about equivalent in size to the outer diameter of the inner clip 18 so that the outer disk 20 can expand slightly to stretch around and fit snugly over the clip 18. The outer diameter of the distal end 28 of the outer disk 20 may be between about 6 cm and 11 cm, while the proximal end 26 of the outer disk 20 may have a flared portion 32 having an outer diameter of between about 10 cm and 15 cm and more preferably 12 cm.

The material thickness of the disk 20 may be about 0.25 in. or 2-4 cm in order to provide sufficient flexibility and pliability to accommodate different and changing diameters of the vaginal canal following childbirth yet also provide enough strength to hold the balloon in place within the uterus. For example, the natural resiliency of the disk 20 allows the disk 20 to expand radially outwardly enough to securely maintain the anchor 12 in place in the vagina 5. As the birth canal contracts back down, the disk 20 can adjust in size to also contract, therefore allowing the anchor 12 to function efficiently and accurately as intended throughout the entirety of a procedure as the dimensions of the patient's anatomy changes. As such, the anchor 12 can be used to retain the tamponade assembly 2 in place across a wide range of patients having differing anatomical dimensions as well as within the same patient when the cervix 7 and vagina 5 change in size immediately following childbirth.

In one example, the disk 20 may be constructed of a material that can conform to the shape, size and configuration of the orifice in which it is to be placed, including the vaginal canal. The disk material is preferably biocompatible and pliable enough to expand and contract with the vaginal wall but rigid enough to retain its general shape and position inside of the vaginal canal. In one example, the disk 20 may be constructed of silicone with a durometer of about 30 D to about 70 D as necessary or desired. The disk 20 may also be constructed of other materials or soft plastics, rubbers, polymers and co-polymers and preferably a material that is relatively soft and/or pliable enough such that it is non-traumatic to the sensitive tissue of the cervix 7 and vagina 5 yet can maintain its overall structure in order to retain the tamponade assembly in position within the uterus 4.

In one example, the disk 20 may be an uninterrupted ring that fully surrounds and is coaxial with the inner clip 18. However, as shown generally in FIGS. 1 and 2, the outer disk 20 may include a slit or opening 34 that is positioned adjacent to or otherwise generally aligned with any slot 23 or gap formed in the ring-like structure of the inner clip 18.

This allows the anchor 12, including the inner clip 18 and outer disk 20 to be snap fitted onto the longitudinal shaft 9 of the catheter 8 together as a unit. The proximal end 26 of the disk 20 may have a flare that extends radially outwardly, such that a flared proximal portion or end 32 of the disk 20 has an outer diameter of about 10 cm to about 15 cm. In one example, the flared proximal end 32 of the disk 20 may be advantageous to aide in retention of the anchor 12 within the vagina 5. Preferably, the disk 20 has a smooth outer surface with generally rounded or curved edges to aide in patient comfort during insertion and removal from the vaginal canal.

As shown in FIGS. 2-6, the disk 20 may further include one or more openings or holes 36 formed therein. The one or more holes 36 may be formed in the flared proximal end 32 of the disk 20. In one example, there may be two holes, three holes or more holes formed in the disk, and in FIGS. 2-6, the disk 20 comprises multiple pairs of holes 36 formed in each of four quadrants equally spaced circumferentially around the flared proximal end 32 of the disk 20. One or more ties or tethers 38 can be threaded or laced through each of the pairs of holes 36 such that the loose ends of the tethers 38 extend outwardly from the proximal end 26 of the outer disk 20. It is contemplated that a single long tether can be threaded through one or more (or all) of the pairs of holes 36, or, alternatively, multiple individual tethers can each be threaded through each of the respective pairs of holes 36. The one or more tethers 38 are long enough to extend outside of the body during use to allow the physician to comfortably and securely grasp the proximal ends 40 of the tethers 38 during removal of the anchor 12 from the vagina 5 upon completion of treatment as described in further detail below.

Figure 10:
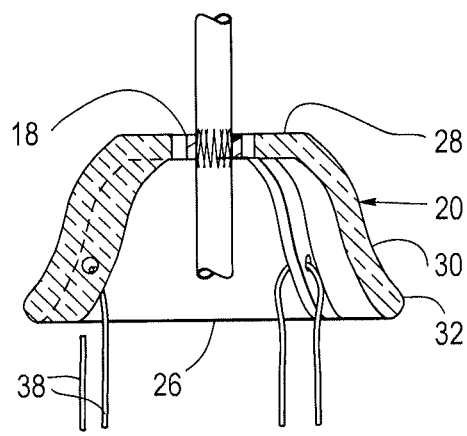
FIG. 10 is a side cross-sectional view of another example of an anchor having internal ribs with multiple tethers secured to the internal ribs.
Figure 11:
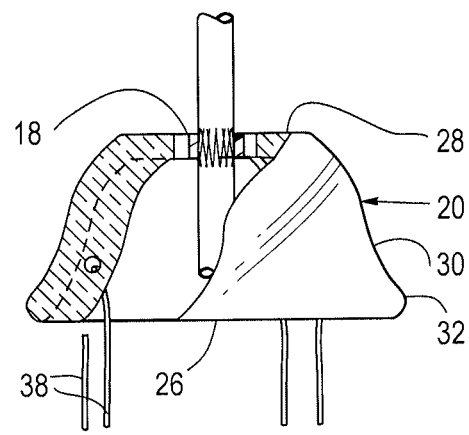
FIG. 11 is a side partial cut-away view of the anchor of FIG. 10 showing tethers secured to internal ribs and a smooth outer surface.

In another example, as shown in FIGS. 10 and 11, the one or more holes or apertures 36 on the anchor 12 for tether attachment could be internal, leaving the exterior of the anchor 12 smooth, to prevent discomfort, abrasion or tissue attachment. More specifically, the outer disk 20 may include one or more internal ribs or protrusions 37. The internal ribs or protrusions 37 can be evenly spaced circumferentially from each other and extend radially inwardly and/or downwardly from an inner surface of the outer disk 20. One or more holes 36 may be formed in the protrusions 37 to allow a tether 38 to be threaded through the holes and attached to the anchor 12.

The tethers 38 may be constructed of a material having enough strength to collapse at least a portion of the outer disk 20 to remove the disk 20 from the patient without risking breakage. In one non-limiting example, the tethers 38 may be constructed of a nylon monofilament, PTFE, Tevdek®, Polydek®, braided plastic fiber or like material to prevent stretching and breakage when the user pulls proximally on the tethers 38 during removal of the anchor 12 from the vagina 5. Preferably, the materials used to construct the anchor 12, including the inner clip 18 and outer disk 20, as well as the materials used to construct the tethers 38 are transparent or at least semi-transparent in order to allow a physician to monitor blood flow that may be occurring behind the device within the cervix 7 and/or vagina 5.

When clipped on the catheter shaft 9 and slid into place within the vagina 5, the natural resiliency of the outer ring 20 of anchor 12 will allow the anchor 12 to expand radially outwardly to its natural state and dimension. As such, the anchor 12 will apply force to the vaginal wall, thus fixing the catheter shaft 9 and balloon 6 in place and substantially preventing dislodgement of the balloon 6 from the uterus 4. The inner diameter of the outer ring 20 also simultaneously presses inwardly upon the inner clip 18, such that, in addition to the roughened texture 11 of the inner surface 19 of the clip 18, the additional inward force upon the inner clip 18 provided by the outer ring 20 further serves to snugly retain the clip 18 upon the catheter shaft 9 and prevent the clip 18 from unwanted sliding or moving from its desired position on the shaft 9.

As previously noted, the rigidity provided to the catheter 8 by the internal stylet 10 prevents longitudinal collapse of the catheter 8, such that at least the portion of the catheter 8 located between the balloon 6 and the anchor 12 will maintain structural integrity and longitudinal length. This prevents longitudinal shrinkage or collapse of the longitudinal catheter shaft 9 when force is exerted on it in either a proximal and/or distal direction, such as in the event that the uterus 4 attempts to "deliver" the balloon 6 through an insufficient cervix 7 (thus exerting pressure on the catheter shaft 9 in a proximal direction) and/or when a physician pushes the catheter 8 into the uterus 4 during insertion (thus exerting pressure on the catheter shaft 9 in a distal direction).

Turning now to FIGS. 1 and 2, use and deployment of the anchor 12 with a uterine tamponade apparatus 2 such as the Bakri® balloon catheter may be as follows. In one example, the uterine tamponade assembly 2 is inserted into a patient and the balloon 6 is suitably positioned within the uterus 4. Optionally, the internal stylet 10 may be inserted into a lumen of the catheter 8, such as into the drainage lumen 16. The distal end 15 of the catheter 8 carrying the tamponade balloon 6 may be inserted trans-vaginally through the cervix 7 (or alternatively inserted through a C-section incision) and into the uterus 4 of a patient in its deflated or radially contracted state. Once the balloon 6 is in its desired position in the uterus 4, it is inflated or otherwise expanded with a physiologically suitable fluid through the inflation lumen 14. The shape of the fully expanded balloon 6 will generally conform to the shape of the interior of the uterus 4, and preferably the lower uterine segment, thus exerting a compressive force against the uterine walls. Once the balloon 6 has at least begun to inflate, the anchor 12 may be snap fitted onto the longitudinal catheter shaft 9 at a location that will, at least initially, remain outside of the patient.

The proximal flared portion or end 32 of the outer disk 20 will face proximally towards the physician performing the procedure. The physician may squeeze the flared proximal end 32 of the outer disk 20 inwardly and/or downwardly while pushing the anchor 12 in a distal direction along the catheter shaft 9 up into the vaginal canal 5 until it has reached an area close to the opening of the cervix 7. The one or more tethers 38 will extend from the proximal end 26 of the outer disk 20 to a location outside of the body. Once the anchor 12 is properly located within the vagina 5, the resiliency of the material of the outer disk 20 allows the disk to expand radially outwardly to its natural resting state to accommodate different and changing diameters of the vaginal canal following childbirth. As such, the anchor 12 is therefore adjustable and/or customizable, in that the outer disk 20 deploys radially outwardly a selected distance so that it can be adjusted to fit with a variety of vaginal diameters depending on a particular patient's anatomy and location of deployment. At the same time, in addition to the roughened inner surface of the inner clip 18 upon the catheter shaft 9, the inner diameter of the outer disk 20 squeezes down on the inner clip 18, thereby also aiding in the retention of the clip 18 in position upon the exterior surface of the longitudinal catheter shaft 9. Pressure from the inflated balloon 6 also serves to provide slight downward (proximal) pressure upon the cervix and vagina 5 thereby also helping to urge the outer disc 20 to flare outward and maintain its position within the vagina 5.

Once the anchor 12 has achieved the desired force against the vaginal wall as determined by the physician, the anchor 12 is thus "locked" in place in the deployed position within the vagina 5. In this way, the balloon 6 is retained in its proper position within the uterine cavity 4 by the anchor 12 resisting and even preventing displacement or dislodgement of the catheter 8 and the balloon 6 carried on the distal end thereof, allowing the apparatus 2 to function as intended for the control and management of PPH and uterine bleeding. Blood or other fluids within the uterus 4 may enter the openings 17 at the distal end 15 of the catheter 8 and drain though the drainage lumen 16 and/or the lumen of the stylet 10. The anchor 12 does not obstruct visualization of the cervix 7 and vagina 5 which allows continued monitoring of the tissues so that the physician may determine whether the bleeding has been controlled or stopped. Furthermore, as shown in FIG. 4, it is also contemplated that the anchor 12 may have one or more drainage holes or apertures 35 formed therein, including but not limited to one or more holes formed in the inner clip 18 and/or the outer disk 20, to allow fluid such as blood to drain there through.

When release and removal of the anchor 12 is desired, the physician may bring together and grasp the proximal end(s) 40 of one or more tethers 38 and pull backwards or proximally on the tethers 38. This action serves to pull the outer edges of the outer disk 20 radially inwardly to thereby collapse at least the flared proximal end 32 of the disk. The reduction of the outer diameter of the outer disk 20 allows the anchor 12 to dislodge from the vagina 5 and then slide backwards in a proximal direction along the catheter shaft 9, thus moving the anchor 12, including the outer disk 20 and inner clip 18 to release the anchor 12 from the vagina 5. Likewise, in an embodiment where the one or more tethers 38 are attached to one or more ribs or protrusions 37, pulling on the proximal ends 40 of the tethers 38 will also cause the protrusions 37 to pull inwardly, thus pulling the outer edges of the outer disk 20 inwardly and downwardly along with the protrusions 37. Again, reduction of the outer diameter of the outer disk 20 combined with the force of pulling proximally on the tethers 38 allows the anchor 12 to dislodge from the vagina 5. If and when uterine bleeding is controlled, the balloon 6 may then be deflated and withdrawn from the uterus 4.

Figure 8:
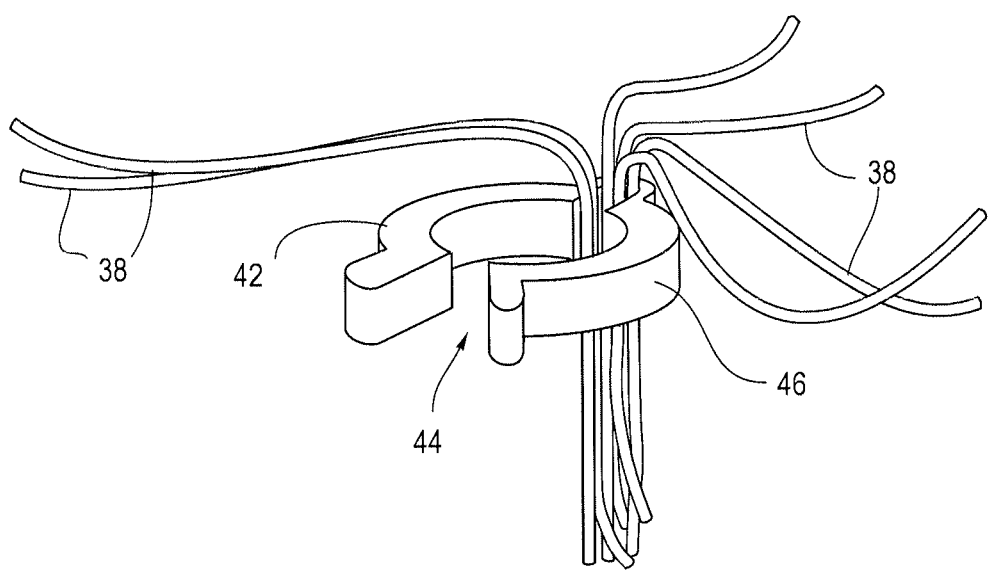
FIG. 8 is an enlarged view of the optional tether attachment ring.

While the one or more tethers 38 may be loose filaments and/or strands extending from the anchor 12 to a location outside of the patient, it is also contemplated that the one or more tethers 38 may extend to an additional or secondary clip 18, such as tether clip 42 as shown in FIGS. 7 and 8. As shown, the one or more tethers 38 may extend from the proximal flared end 32 of the outer disk 20 to the tether clip 42 which is preferably located at a position on the catheter shaft 9 outside of the patient's body. The tether clip 42 is longitudinally slideable along the shaft 9. In one example, the tether clip 42 may be a ring-like structure that fully surrounds or encircles the shaft 9 of the catheter 8 and can be threaded onto one end of the catheter 8 and pushed longitudinally or slid into position at a desired location on the catheter 8 for use. Alternatively, the tether clip 42 may fully or at least partially surround the shaft 9 of the catheter 8 and may include a small opening or slot 44 that allows the tether clip 42 to be snap fitted on (and off) of the catheter 8 from the side at any desirable location along the length of the shaft 9 of the catheter 8. The location of tether clip 42 may be adjusted to hold the tethers 38 taught and organized to prevent entanglement, but not so tight that it collapses the flared proximal end 32 of the outer disk 20 prematurely.

When the physician desires to remove the anchor 12 from the vagina 5, the physician may grip the outer surface 46 of the tether clip 42 and gently pull backwards in a proximal direction. This action causes the tether clip 42 to slide longitudinally in a proximal direction (towards the physician) along the shaft 9 of the catheter 8, thus pulling the one or more tethers 38 proximally. Similar to the pulling force provided by the physician described above when pulling on the tethers directly, the pulling force on the tether clip 42 causes the tethers 38 to become tensioned in a rearward or proximal direction to thereby pull the outer edges of the disk 20 radially inwardly to thereby collapse at least the flared proximal end 32 of the outer disk 20. The reduction of the outer diameter of the outer disk 20 allows the anchor 12 to then slide backwards in a proximal direction along the catheter shaft 9, thus moving the anchor 12, including the outer disk 20 and inner clip 18, to release the anchor 12 from the vagina 5. The balloon 6 may then be deflated as necessary and desired and the tamponade assembly removed from the patient upon completion of the procedure. Preferably, the balloon could be deflated before the anchor 12 is removed to prevent premature displacement of the balloon 6 into the cervix 7. The stylet 10 may also be utilized to stabilize, support and/or guide the tamponade assembly 2 during removal from the patient.

Figure 9:
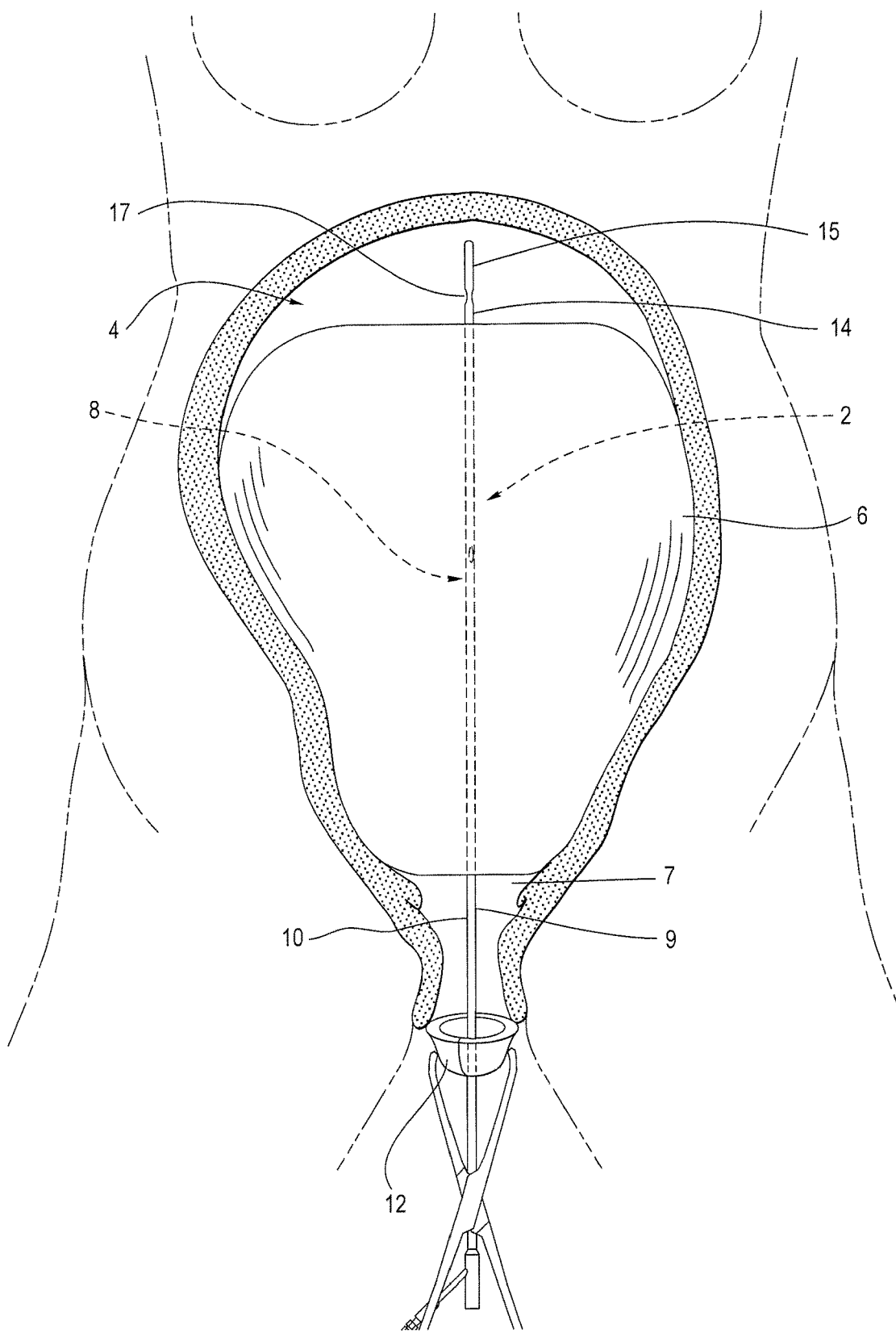
FIG. 9 is a front view of a patient's anatomy showing a uterine tamponade device and another example of an anchor deployed in the vagina in a different orientation for anchoring the tamponade device in place within the uterine cavity and one method of removal of the anchor using a grasping device.
Figure 12:
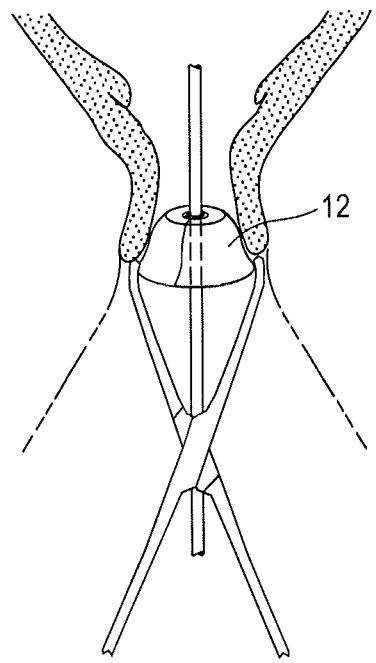
FIG. 12 is an enlarged perspective view of another example of an anchor secured to a catheter shaft and deployed in the vagina and one method of removal of the anchor using a grasping device.

In another example, as shown generally in FIG. 9 and FIG. 12, the tethers 38 attached to the anchor 12 may be omitted. Instead, removal of the anchor 12 could be accomplished through the use of a grasping device such as forceps, by grasping the edges of the outer disk 20 and pinching the anchor 12 to allow the clip 18 to release from the shaft 9 of the catheter 8 and be removed. As such, the anchor 12 could be oriented "upside down" with the flared end 32 facing upward or in a distal-facing direction such that the flared end 32 of the anchor 12 cradles the base or proximal end of the balloon 6 as shown in FIG. 9. Alternatively, the anchor 12 with the tethers 38 absent, may be oriented in the manner shown generally in FIG. 1 and FIG. 12, in which the flared proximal end 32 of the outer disk 20 faces downwardly or in a proximal-facing direction. In either orientation of the anchor 12, a grasping device such as forceps can be used to grasp the anchor 12 to allow the anchor 12 to be dislodged and removed from the patient.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. A uterine tamponade assembly comprising:
   a catheter comprising a longitudinal body having a proximal end and a distal end and at least one drainage lumen extending there between;
   an expandable tamponade device located at the distal end of the catheter, the tamponade device configured for insertion into a body cavity;

an anchor for securing the assembly within the body cavity, the anchor comprising at least one clip removably attached to the longitudinal catheter body, at least one outer disk disposed about the at least one clip;

wherein the at least one outer disk comprises a proximal end and a distal end and wherein an outer diameter of the proximal end of the at least one outer disk is greater than an outer diameter of the distal end of the at least one outer disk; and wherein the at least one outer disk comprises one or more apertures for allowing fluid to drain therethrough; and wherein the at least one clip is located within an opening formed in the distal end of the at least one outer disk such that the at least one clip is attached to the longitudinal catheter body at the distal end of the at least one outer disk.

2. The assembly of claim 1 wherein the tamponade device comprises an inflatable balloon configured for expansion within the body cavity.

3. The assembly of claim 1 wherein the at least one outer disk is concentric with the at least one clip.

4. The assembly of claim 1 wherein the anchor is configured for insertion and expansion in the vaginal canal.

5. The assembly of claim 1 further comprising a stylet extending longitudinally within the drainage lumen of the catheter.

6. The assembly of claim 5 wherein the stylet comprises a proximal end and a distal end and a lumen extending there between.

7. The assembly of claim 1 wherein the at least one clip at least partially circumferentially surrounds the longitudinal body of the catheter.

8. The assembly of claim 1 wherein an inner surface of the at least one clip comprises a gripping surface adapted to enhance traction between the inner surface of the at least one clip and the longitudinal body of the catheter.

9. The assembly of claim 1 wherein the at least one clip is a ring-like structure with at least one slot configured to allow the at least one clip to snap onto the longitudinal catheter body from the side.

10. The assembly of claim 9 wherein the at least one outer disk comprises a slit that is substantially aligned with the at least one slot formed in the clip.

11. The assembly of claim 1 wherein the anchor is longitudinally slideable on the catheter body.

12. The assembly of claim 1 wherein the outer disk comprises a durometer of approximately 30 D to approximately 70 D.

* * * * *